United States Patent [19]
Garcia Y Bellon et al.

[11] Patent Number: 5,155,096
[45] Date of Patent: * Oct. 13, 1992

[54] METHOD FOR POTENTIATION OF A THERAPEUTIC AGENT

[76] Inventors: Donato P. Garcia Y Bellon, Ponciano Arriaga #28 PB, Col. Centro, Cuauhtemoc, Mexico, 06030; Donato P. Garcia, Jr., 4558 Blvd. Agua Cliente Col. Aviacion, Tijuana, Mexico, 22420; Steven G. Ayre, 483 First St., Antioch, Ill. 60002

[*] Notice: The portion of the term of this patent subsequent to Nov. 20, 2007 has been disclaimed.

[21] Appl. No.: 615,621

[22] Filed: Nov. 19, 1990

Related U.S. Application Data

[63] Continuation-in-part of Ser. No. 077,833, Jul. 27, 1987, Pat. No. 4,971,951.

[51] Int. Cl.$^5$ ............................................. A61K 37/26
[52] U.S. Cl. ......................................... 514/3; 514/4; 514/825; 514/885; 514/886; 514/893; 514/966; 514/967
[58] Field of Search ............... 514/3, 4; 424/825, 885, 424/886, 893, 966, 967

[56] References Cited

U.S. PATENT DOCUMENTS 4,971,951 11/1990 Garcia y Bellon et al. ............ 514/3

*Primary Examiner*—Nathan M. Nutter
*Attorney, Agent, or Firm*—Melvin K. Silverman

[57] ABSTRACT

The invention relates to a method for potentiation of a therapeutic agent, the method comprising the steps of administering an effective dose of insulin to induce to hypoglycemia; administering a pre-determined dose of a therapeutic agent; and administering a pre-determined dose of glucose sufficient to substantially neutralize the hypoglycemia. As an adjuvant system, the instant invention constitutes the combination of a quantity of insulin in the range of one to four units per 10 kilograms of body weight; a pre-determined quantity of the therapeutic agent; and glucose in the form of a hypertonic solution between about 5% and about 50% glucose, the volume of the solution being in the range of about 10 cubic centimeters to about 100 cubic centimeters. The inventive method is known as Insulin Potentiation Therapy (IPT).

31 Claims, No Drawings

METHOD FOR POTENTIATION OF A THERAPEUTIC AGENT

REFERENCE TO RELATED APPLICATION

This case is a continuation in part of application Ser. No. 07/077,833, filed Jul. 27, 1987, now U.S. Pat. No. 4,971,951.

BACKGROUND OF THE INVENTION

The hormone insulin is recognized as having actions that affect the trans-membrane transport of different substances, particularly glucose, into numerous different kinds of cells of the human body.

Insulin is a large polyteptide molecule with a molecular weight of 5808. It consists of a so-called A Chain and a so-called B Chain, connected together by two disulfide bridges. The hormone insulin is produced in the beta cells of the pancreas, and the stimulus for its secretion into the bloodstream is a function of an increase in blood glucose concentration.

Its action on the liver, adipose tissue, and skeletal muscle have all been studied in the literature in great detail, and it is now recognized that insulin also affects a wide variety of tissues in addition to these.

Apart from its membrane transport of glucose, insulin also regulates transport of some amino acids, certain fatty acids, the minerals potassium and magnesium, and certain monosaccharides. Further, it performs a mediation function by regulating the formation of macromolecules which are used in cell structure, cell energy storage, and the regulation of many cell functions. More particularly, it is known that glucose stimulates glycogenolysis, lipogenesis, proteogenesis, and nucleic acid synthesis. It also increase glucose oxidation and magnesium-activated sodium-potassium ATPase activity.

It is further known that there is a single mechanism involved in the initiation of all of the above biological affects and, particularly, this mechanism is the interaction of the hormone insulin with its specific cell receptor. The insulin receptor consists of two alpha subunits, each of molecular weight 135,000 and two beta subunits, each having a molecular weight of 95,000, which are linked together by disulfide bonds. The alpha unit is predominantly located upon the outer surface of the cell membrane, and the insulin binding/linkage domain is located there. The transmembrane beta unit contains tyrosine kinase activity on its cytoplasmic domain that results in rapid receptor autophosphorylation, that is, effective absorption of the beta subunit into the cell. Activation of the kinase toward exogenous substrates of the cell is, it appears, preceded by this insulin-dependent autophosphorylation reaction of the beta subunit. Action on other cellular substraites ultimately leads to the expression of the full range of insulin actions at the cellular level. See Schnetzler, Rubin, and Pilch. Structural Requirements for the Transmembrane Activation of the Insulin Receptor Kinase. J Biol Chem 261:15281-15287, 1986.

After insulin binds to the receptor with activation of the kinase, followed by receptor autophosphorylation, the insulin-receptor combination is endocytosed (absorbed) into the cell cytoplasm. This phenomena accounts for the down-regulation of insulin receptor activity within the blood that ensues following insulin stimulation. With this endocytosis, a variety of events may then take place. Insulin disassociates from the receptor and, following fusion of the endocytotic vesicle with cellular lysomes, it is degraded by lysomal enzymes. The free receptor may then itself be degraded by the lysomal enzymes, or it may recycle back to the surface (substrate) of the cell membrane. Finally, the free phosphorylated receptor may proceed to activate other substrates in the cytoplasm or may activate particular cellular organelles, e.g., the golgi apparatus and the nucleus, to produce the many cell changes referred to above. See Heidenreich and Olefsky. Metabolism of Insulin Receptors: Molecular Bases for Insulin Action. Page 163, Plenum Press, New York, 1985.

The most commonly recognized action of insulin is that of lowering blood glucose. This is accomplished via a process of facilitated diffusion across cell membranes. It has been hypothesized that the mechanism of this facilitated diffusion involves the translocation of a glucose transport protein from the cytoplasm out to the cell membrane (the exterior substrate). This translocation process involves the fusion of intracytoplasmic vesicles with the membrane of the cell. These vesicles contain the glucose transport protein in their enclosing membranes. Once exteriorized on the cell surface, the transport proteins of the vesicles serve as channels for glucose to enter the cell. This particular protein has been identified as a 40,000 molecular weight moiety that is associated with the golgi apparatus. See Burdett, Beeler and clip. Distribution of Glucose Transporters in Insulin Receptors in the Plasma Membrane and Transverse Tubules of Skeletal Muscle. Arch 8 Biochem Biopys 253:279-286, 1987.

The above process of translocation is reversible via endocytotsis of the membrane fragment containing said transport proteins, thus reconstituting the intra cytoplasmic vesicles. The whole activity of the glucose transport proteins is dependent upon metabolic energy and is independent of protein synthesis. See Kono, Translocation Hypothesis of Insulin Action on Glucose Transport. Federation Proc 43:2256-2257, 1984. The precise nature of the signal or messenger through which insulin turns this process on and off remains to be fully explained.

It is known that insulin receptors are widely distributed in mammalian organisms, there being in the range of 100 to 100,000 receptors per cell in different tissues. Rarely do any cells have no receptors at all. See Rosen. After Insulin Binds. Science 273:1452-1457, 1987.

A number of malignant neoplastic tissues have also been found to have a plentiful supply of insulin receptors, see Wong and Holdaway. Insulin Binding by Normal and Neoplastic: Tissue. Int J Cancer 35:335-341, 1985, perhaps reflecting cancer cell metabolism and the enhanced need that malignant cells have for glucose (see Cone, U.S. Pat. No. 4,935,450). Insulin may also play a role in the stimulation of cancer cell growth. See Myal, Shiu, Bhomic, and Bala. Receptor Binding and Growth Promoting Activity of Insulin-like Growth Factors and Human Breast Cancer Cells. Cancer Research 44:5486-5490, 1984.) A number of different cancers have been found to actually produce and secrete their own insulin. See Shamas, Dhurandhar, Blackar, Insulin-secreating Bronchial Carcinoid Tumor with Widespread Netastases. Am J Med 44:632-637,. And Pavelic, Popovic. Insulin and Glucogon Secretion by Renal Adeno-Carcinoma. Cancer 48:98-100, 1981.

Investigation of many of the actions of insulin upon insulin receptors in numerous species has demonstrated that the properties of insulin receptors in mammalian tissue are remarkably similar, irrespective of cell type. This being so, it may be anticipated that what the activated insulin/insulin-receptor complex does in one tissue, it will do in all. This would of course be dependent upon the existence of the necessary metabolic machinery within a particular tissue to react to insulin activation. It has been found that not all tissues are equally endowed in such regard. For example, the brain is a tissue which does not have insulin receptors, but which does have an insulin-dependent glucose transport mechanism. More particularly, insulin receptors are found both on the capillary endothelium of the blood brain barrier (BBB) as well as upon the glial elements within the substance of the brain. These receptors do not seem to play any role, in conjunction with insulin, in the transmembrane transport of glucose which is essential to proper brain metabolism. Rather, the capillary endothelium of the BBB has its own unique transport system for glucose, as well as for a number of other nutrient transport system substances such as choline, adenine, adenosine, lactate, glutamate, phenylalanine, and arginine. See Pardridge. Receptor-Mediated Peptide Transport Through the Blood-Brain Barrier. Endocrine Reviews 7:314–330, 1986.

The composition of this meager interstitial fluid of the brain is carefully controlled by the very selective functioning of the BBB. Having access to this space, the substances then have free access to the brain cells.

The glucose transport system in the brain responds to chronic changes in blood glucose levels. That is, the system is up-regulated during periods of hyperglycemia, and in like fashion is down-regulated during prolonged periods of hypoglycemia, such as can occur with poorly controlled diabetes. In the context of the instant invention, glucose transport across the BBB is insulin-independent, and yet insulin receptors are found on the same BBB capillary endothelium which carries the glucose transport system. This insulin transport system is just one of a number of peptide transport systems found on the BBB. Others carry the insulin-like growth factors I and II and transferrin. See Pardridge, supra. The BBB insulin receptor is a glycoprotein having structural characteristics typical of the insulin receptor in peripheral tissues. It may be part of a combined endocytosis and, exocytosis systems, that is, a transcytosis system for the transport of the peptide of focus through the BBB in humans. The transcytosis of insulin through the human BBB would, it appears, allow for distribution and circulation insulin into brain interstitial areas and insulin action upon brain cells. Through a non-receptor mechanism.

In skeletal muscle, insulin has been shown to deliver enzyme-insulin-albumin conjugates into the cell. This entire complex, it has been determined, is transported into the cell by a process resembling receptor-mediated endocytosis, and the enzyme-albumin-insulin complex is maintained by its enzymatic activity and its ability to bind antibodies to insulin. See Poznansky, Singh, Singh, and Fantus. Insulin: Carrier Potential for Enzyme and Drug Therapy. Science 223:1304–1306, 1984.

The instant invention reflects an elaboration of the above principles and, more specifically, those principals and methods set forth in our U.S. Pat. No. 4,971,951. In addition to said patent, other patented prior art has recognized the importance of the role of insulin as a carrier, adjuvant, or agent to enhance the absorption or to potentiate the effect of drugs administered to patients for the treatment of specific diseases. More particularly, U.S. Pat. No. 2,145,869, discloses a composition including insulin and glucose for the treatment of syphilis. Further, U.S. Pat. No. 4,196,196 (1980) to Tiholiz discloses a composition of insulin, glucose and magnesium dipotassium ethyline, diamine tetraacetic acid to enhance tissue perfusion and to facilitate a divalent-monovalent cation gradient. The general value and significance, in cancer treatment, of such a cation gradient, however facilitated, is recognized in U.S. Pat. No. 4,018,649 (1977) to Cone, entitled Process and Control of Cell Division.

A further U.S. Patent, namely, U.S. Pat. No. 4,277,465 (1981) to Kamada, teaches the use of an enamine derivative molecularly linked to insulin to facilitate its therapeutic absorption across the digestive tract.

The importance of insulin activity messengers is set forth in U.S. Pat. No. 4,839,466 (1989) to Saltiel.

The importance of insulin in the metabolism of malignant cells is, as noted above, recognized and discussed in U.S. Pat. No. 4,935,450 (1990) to Cone, entitled Cancer Therapy System for Effecting Oncolysis of Malignant Neoplasms.

Our above referenced U.S. Pat. No. 4,971,951 teaches a method of treatment of viral diseases including cancer and AIDS. The present invention is concerned with a broader method and means of systemic adjuvenation for potentiation of a broad range of therapeutic agents. In this sense, the instant invention may be viewed as an improvement of the invention of our said earlier U.S. patent.

SUMMARY OF THE INVENTION

The invention relates to a method for potentiation of a therapeutic agent, the method comprising the steps of administering an effective dose of insulin to induce to hypoglycemia; administering a pharmacologically effective dose of a therapeutic agent; and administering a pharmacologically effective dose of glucose sufficient to substantially neutralize said hypoglycimia. As an adjuvant system, the instant invention comprises the combination of a quantity of insulin in the range of one to four units per 10 kilograms of body weight; a predetermined quantity of the therapeutic agent; and glucose in the form of a hypertonic solution between about 5% and about 50% glucose, the volume of said solution being in the range of about 10 cubic centimeters to about 100 cubic centimeters. The inventive method is known as Insulin Potentiation Therapy (IPT).

A wide variety of therapeutic agents across a spectrum of disease classes may be utilized in accordance with the present inventive method and system.

Particularly, the instant invention relates to a novel method and means of treatment of diseases, on a intracellular level, by inducing hypoglocymia by administration of insulin and the subsequent administration, during the state of hypoglocymia, of glucose and a specific prescribed drug, or combinations thereof, directed to the specific disease.

The invention also relates to a method and means of treatment of diseases by administration of drugs, in lower dosages than would ordinarily be required for effective treatment in the absence of the insulin/glucose system, in accordance with the present invention.

Accordingly, an object of the present invention is to provide a method of systemic adjuvenation that will enhance the absorbability and, thereby, intracellular delivery, of therapeutic agents.

It is a further object to provide a therapeutic system of the above type.

It is yet further object to provide a method and means having an enhanced effectiveness in the treatment of a wide variety of classes of illnesses, using a spectrum of drug types, in many forms of administration.

The above and yet further objects and advantages of the invention will become apparent from the Detailed Description of the Invention and Claims appended herewith.

DETAILED DESCRIPTION OF THE INVENTION

The initial step in the inventive method constitutes the administration of an effective dose of insulin to induce hypoglocemia. This, through experimentation, has been determined to be in the range of 1-4 units of insulin per 10 kilograms of body weight. In a preferred embodiment, crystaline insulin in bottles of 40 units per milliliter is employed.

In a second step, a predetermined and effective dose of a therapeutic agent is administered, preferably together with a nutrient combination, for example, a vitamin B complex or an electrolyte normalization solution such as a Ringer sodium lactate solution.

It is to be noted that said therapeutic agent administering step may comprise, depending upon the absorption characteristic of the therapeutic agent absorbed, any one of the following:

a. In the case of a slowly metabolically absorbed agent, (that is, about one-half hour), administration of the therapeutic agent occurs prior to the insulin administration step so that the level of such agent in the blood is optimized by the time that the hypoglocemia is induced following said insulin administering step.

b. The therapeutic agent may be administered contemporaneously with the insulin administration, or shortly thereafter, as hypoglycemia develops.

c. In the case of a rapidly metabolically absorbed agent, (that is, absorption in minutes) administration of the therapeutic agent occurs subsequent to the onset of hypoglocymia. When this occurs, the step of administering glucose (to neutralize the hypoglocymia) occurs usually contemporaneously with, or shortly after, the administration of the therapeutic agent.

As is noted above, certain nutrient combinations may be employed together with the use of the therapeutic agent to achieve one or more ends. More particularly, a vitamin B complex, such as a combination of Vitamins B1, B2, and B6 may be used. It is believed that these vitamins act as co-enzymes to achieve detoxification and to accelerate the ATP synthesis through the Krebs cycle. Also, they assist in enhanced levels of aerobic metabolism of glucose.

Other nutrients have also been found to be valuable in administration with the therapeutic agent. For example, vitamin C and iron-dextrose colloids are most helpful.

Further, we have developed a specific nutritional combination consisting of 100 mg of Vitamin B12, 100 mg of thiamine, 50 mg of pyridoxine, and 5 mg of adenosine triphosphate (ATD) which we have found to comprise a particularly effective vitamin B complex for use together with specific therapeutic agents.

We have also discovered that equalization of electrolytes, that is, normalization of the intracellular ionic hierarchy, is important in treatment of many diseases, particularly cancer, as is recognized by Cone in U.S. Pat. No. 4,018,649 (1977). Normalization of electrolytes may be facilitated by various means including, as above noted, the use of an intravenous Ringer sodium lactate.

Also, we have found that the use of oxygen, in various forms, is useful in certain expressions of IPT. That is, in addition to direct respiratory use of oxygen during therapy, we have discovered that provision of increased oxygen through other means, such as through the use of dichloroethanate of di-isopropylammonium, operates to increase oxygenation through vasodilation and through the stimulation of mitochondrial oxireductases. Accordingly, it is to be appreciated that this and other means for providing enhanced oxygen to cells during the step of administration of the therapeutic agent subsequent to the induction of hypoglocymia, comprises an important embodiment of the instant inventive method and system.

It has been also found that, in many patients, the application of a cathartic before treatment is most useful.

The administration of insulin in clinical practice is typically intravenous. In other embodiments and, particularly, as the state-of-the-art of administration of insulin is improved, insulin administration may be in other forms including oral, intramuscular, transcutaneous, respiratory, transdermal, sublingual and nasal. Many recent developments in the modification of the insulin molecule to permit its linkage to other molecules has made possible remarkable advances in non-intravenous means of insulin delivery including, without limitation, oral nasal and sublingual delivery of insulin. See U.S. Pat. Nos. 4,153,689 and 4,849,405. Accordingly, the instant invention is to be understood as, extending to the use or application of insulin however delivered to the bloodstream.

The step of glucose administration, must be sufficient to substantially neutralize the hypoglycemia caused by the initial administration of insulin. It more particularly comprises the administration of between about 10 about 100 cubic centimeters of between about 5 and about 50% hypertonic glucose solution. The hypertonic glucose solution is important in that glucose, in such solution, must possess an osmotic characteristic which is compatible with that of blood. Accordingly, the desired effort of the glucose administration is assured by maximizing the compatibility of the administered glucose solution with the osmotic pressure and another characteristics of the blood.

It is to be found that Insulin Potentiation Therapy (IPT) is applicable in the treatment of a variety of disorders and diseases. A cross-section of such IPT treatments are now described in the following areas and clinical cases:

Allergic Disorders

Case 1: Angioendema

A 19 year-old hispanic female suffered from frequent skin eruptions since she was 13 years old. This included welts 3 mm in diameter, and pruritus and edema localized to her hands, eyelids, and mucous membranes of the upper sinuses. These conditions combined to produce considerable respiratory distress. She was diagnosed as having asthma, however, medication prescribed by other physicians was not helpful. Finally, she was diagnosed as having chronic angioedema, also known as urticaria.

Her IPT therapy consisted of three IPT treatments, each comprising:

1. An enema of 900 ml of warm tap temperature water having therein 100 ml of lactulose syrup.
2. Twelve units insulin administered by intravenous bolus. (The term "bolus" means at one time, or by one injection.)
3. Oral administration of tablets diphenhydramine 50 mg; prednisone 15 mg; and Senokot tablets (Columbia Labs).
4. Intramuscular administration of 1 ml liver extract.
5. Intravenous administration of Vitamin C 0.5 gm; calcium gluconate 2 ml; B-complex-1 ml; and epinephrine-1:1000, 0.3 ml, epinephrine is a form of adrenalin.

Between the three IPT treatments she received Senokot tablets (a laxative) at bedtime; diphenhyhdramine 50 mg every six hours; Vitamin A 50,000 IU; and Vitamin E 100 units.

Since completion of the above course of treatment, she has remained symptom free for a number of years.

In other allergic disorders, we have found that antihistamine may be successfully used and, particularly, in cases of allergic disorder have utilized clemizole hydrochloride in dosages of 100 mg in 1 ml distilled water administered intravenously and 0.3 ml administered intramuscularly. This compound operates as a dexamethazone detoxifier. This medication is sold by Schering Plough under the name Allecur.

Bacterial Diseases

Case 2: Pharyngeal Infection

A 35 year-old hispanic male developed a malaise, weakness, myalgias, arthralgias, headaches and anorexia. Upon examination, it was determined that he had fever of 100.8 F. and had chills and sweating. He was diagnosed as having a pharyngeal infection caused by a Group A b-hemolytic streptococcus.

The IPT treatment consisted of two specific treatment sessions, each comprising:

1. Enema of 900 ml warm tap water with 100 ml of lactulose syrup.
2. Insulin 21 units intravenous bolus.
3. Oral: aspirin 700 mg.
4. Intramuscular: liver extract 1 ml; and procaine penicillin 600,000 units.
5. Intravensous: Vitamin C 1,000 grains; calcium gluconate 5 ml; and Vitamin B complex 1 ml.

In between treatments the patient took aspirin of 700 mg every 8 hours and erythromycin 0.5 gms every 12 hours for 7 days.

Ten days after discharge from the second treatment a pharyngeal culture was determined to be free of the streptococcus bacteria.

Case 3: Pneumococcal Pneumonia

A 49 year old male suddenly developed shaking, chills, sharp pain in his right thorax, cough with viscous sputum, fever 101.3 F., headache and nausea. He was diagnosed as having pneumococcal pneumonia.

His IPT treatment consisted of four separate treatments each comprising:

1. Enema 900 ml of warm tap water with 100 ml lactose syrup.
2. Insulin 22 units intravenous bolus.
3. Oral: Senokot (a laxative) 2 tablets; and ketotifeno 1 mg. Ketotifeno is known in the United States as kitotifen hydrogen fumarte.
4. Intramuscular: liver extract 1 ml; gadital enzyme 1 cc; and penicillin G 600,000 units. Gadital is a tradename of Italmex Inc.
5. Intravenous: Vitamin C 2,000 milligrams and calcium gluconate 5 ml.

In between treatments he was provided with Metamucil 11 grams at bedtime and Senokot tablets at bedtime. Metamucil is a Procter & Gamble product comprising psyllium fiber. Erythromycin of 500 mg was taken every six hours for seven days as was 50,000 units of vitamin A.

In 7 days, he was completely recovered.

IPT has been found to operate positively with other antibiotics including ampicillin and leucomycine.

Also, in the case of certain traumas to the skin, e.g., burns, Madribon has been used. Madribon is a Roche product comprising sulfadionethovine. This agent has been found, when used in combination with antibiotics and IPT, to assist in healing of skin and other tissue trauma.

Cardiovascular Disorders

Case 4: Varicose Veins

A 52 year old female had suffered from dilated tortuous superficial veins of both lower limbs. After a minor trauma she developed an ulcer of approximately 2 centimeters diameter upon her left ankle, including eczema, induration and pigmentation around the ulcer. She received several treatments of conventional type but the pain and ulcer recurred about once every 16 months. She was diagnosed as having varicose veins, however, refused surgical treatment of a conventional nature.

Her IPT treatment consisted of six treatments each comprising:

1. Enema: 900 ml warm water with 100 ml lactulose syrup.
2. Insulin 18 units intravenous bolus.
3. Oral: Naftidrofuryloxalate 200 mg; Senokot 2 tablets; Boldodrenal 0.5 gr; (Infan) and diosmine 2 tablets Dalfon (Servier)
4. Intramuscular: liver estract 1 mg; and sodium dichlorethanate 75 mg.
5. Intravenous: Vitamin C 2,000 mg; calcium gluconate 5 ml; B-complex 1 ml; and naftidrofuryloxalate 50 mg.

In between treatments she was given Metamucil 11 gm at bedtime; Senokot 2 tablets at bedtime; daflon 2 tablets every 8 hours; naftidrofuryloxalate 200 mg once a day; Vitamin A 25,000 units; vitamin E 100 units; varigel gel (Andre Bigeaux) locally every 8 hours to the veins.

After her six treatments which averaged one every five days, her ulcer had disappeared and she has since remained symptom free.

Gastrointestinal Disorders

Case 5: Duodenal Ulcer

A 35 year old male exhibited symptoms of turning in his stomach, typically experienced in mid morning. The symptoms were relieved by food, however, recurred four hours after every meal. Some nights the pain awakened him at about 2 AM. This condition would last several weeks, disappear for some weeks, and then recur without apparent reason. He was diagnosed as having a duodenal ulcer.

His IPT treatment consisted of three treatments comprising the following:

1. Enema of 900 ml of warm tap water with 100 ml of lactulose syrup.
2. Insulin of 19 units intravenous bolus.

3. Oral: Senokot 1 tablet, and aluminum hydroxide 20 ml.

4. Intramuscular: liver extract 1 ml; and netoclopramide 50 mg.

5. Intravenous: Cimetidine 300 mg; and calcium gluconate 5 ml

In between treatments he was given Metamucil 11 gm at bedtime and 2 Senokot tablets. He was also given Cimetidine 300 mg every 8 hours for the first 8 weeks and then 800 mg once a day for 4 weeks more. He received one IPT treatment weekly. Following his discharge, after 8 weeks, he recovered completely and no recurrence of his duodenal ulcer has occurred.

We have found that IPT can be successfully used with a wide variety of gastrointestinal disorders and that numerous therapeutic agents can be employed. For example, in treatment of gastritis and gastro duodenal ulcers, we have employed nopoxamine lauryl sulphate 2.5 mg; galactant sulphate 200 mg; and basic aluminum amino acetate in chewable form. We have combined the above and have used the same both in the intravenous administration of insulin step of IPT, and orally to the patient between treatments.

Also in the treatment of gastro duodenal ulcers we have made use of geranyl pharneylacetate 50 mg in a dosage of 0.3 ml applied intramuscularly.

Also, in the treatment of ulcers, use has been made of amino acid complexes as one of the therapeutic agents.

In the treatment of other gastro intestinal disorders we have found that the effect of both herbal and conventional medications is potentiated. For example, stabilization of the digestive tract may, with IPT, be achieved with use of a dry artichoke extract 2 gms in combination with a dry boldo extract 2 gms, mixed with magnesium sulphate 19 gms. This mixture, in 100 gm of water, may be taken in a dose of one teaspoon orally between IPT treatments for digestive problems.

Further, in the use of IPT in digestive problems, we have developed a system consisting of the combination of pancreatine 175 mg, hemicelulase 50 mg, bile extract from ox 25 mg, and dimeticone, 25 mg. We have used this mixture both with IPT and in between treatments in a tablet form to stabilize the digestive system.

It is to be understood that in the step insulin administration of IPT that the range of administration of about one to four units of insulin per 10 kilograms of body weights refers to units intravenous bolus.

Gynecological Disorders

Case 6: Gonorrhea

A 22 year old hispanic female was presented with severe lower abdominal pain with nausea and vomiting. She had a prevalent vaginal discharge and reported menstrual irregularities. She was diagnosed as having acute gonorrhea salpingitis.

Her treatment consisted of three IPT treatments, each comprising:

1. Enema of 900 ml of warm tap water with 100 ml of lactulose.

2. Insulin 13 units intravenous bolus.

3. Oral: aspirin 600 mg and Senokot tablets.

4. Intramuscular: liver extract 1 cc; and penicillin G 1,200,000 units.

5. Intravenous: Vitamin C, 2 gms; calcium gluconate 5 ml; dextrevit phosphorilate 1 cc; and dextrose 50% solution 20 cc. Dextrevit phosphorilate is a mixture in solution of glucose, fructose, Vitamins B-1, B-2, B-6, and C, acetyl co-enzyme, DPN and ATP.

In between treatments she was given Senokot tablets at bedtime with Metamucil 11 gms. She was also given ampicillin 500 mg every six hours for 10 days.

At the end of the first IPT treatment the patient reported that the pain in her abdomen had completely disappeared. After the third IPT treatment she was symptom free and has remained such.

Heptic and Biliary Disorders

Case 7: Gall Stones

A 46 year old female complained of recurrent abdominal pain exacerbated by indigestion of fatty foods. She also complained of bloating, belching and intolerance of fat foods. The pain experienced was localized to the right upper abdomen and right shoulder. An ultrasonogram revealed the presence of several stones in her gall bladder. She refused surgery.

The IPT treatment consisted of seven IPT treatments, each comprising the following:

1. Enema 900 ml warm tap water with 100 ml lactulose syrup.

2. Insulin 19 units intravenous bolus.

4. Oral: two Senokot tablets; chenodeoydeoxycholic acid 250 mg; and panclasa two tablets (Atlantis).

4. Intramuscular: liver extract 1 ml; and netoclopramide 50 mg.

5. Intravenous: cimetidine 300 mg.

In between treatments she was given Metamucil 11 gms at bedtime with Senokot 2 tablets. She was also given cimetidine 800 mg once a day for 4 weeks and chenodoexycholic acid 1,000 mg a day for six months. After seven treatments, another ultrasonogram showed only bile mud in her gall bladder and all stones in the gall bladder had disappeared. She is recovered and no recurrence has occurred.

We have found that IPT may be advantageously used with a wide variety of liver related ailments, many of which are the result of toxins in the body as may be the case of conditions of alcoholism and drug abuse. In such detoxification we have successfully made use of carbomoylcholine chloride 2 mg tablets and in ampules of 0.25 mg per milliliter each. The same may be administered orally in tablets or in 0.3 ml intramuscularly. Alternatively, in detoxification of the body, we have successfully used the combination of peptone 5 gms; magnesium sulphate 5 gms; boldo extract 5 gms; and dihydrochloric acid 5 gms.

In addition to the use of various liver extracts in combination with certain nutrients, we have further made use of polyhydroxyflavininol to aid the functioning of the liver and in general detoxification of the body.

IPT, it should be noted, has been used successfully in various treatments for the stimulation of the auto immune system. At a first level, the above described use of IPT in detoxification of patients will, inherently, function to strengthen the immunologic system. Accordingly, many of the above treatments may be used in tandem with IPT cancer directed treatments, below described, and in our U.S. Pat. No. 4,971,951, to both stimulate the immune system and destroy cancer cells.

We have found that the action of ascorbic acid (Vitamin C) can be potentiated, to the benefit of the immune system, when used with IPT.

Further, the use of gamma globulin, at 165 mg has been found to be most useful, in combination with IPT, in stimulating immune system responses. Therefore, such immune system applications of IPT are of value across a wide range of diseases including, as above noted, cancer and, as well, other immunologic disorders including notably AIDS.

Neurologic Disorders

Case 8: Epilepsy

A 24 year old male presented a history of convulsive seizures beginning, in each seizure, with loss of consciousness and jerking of all extremities, this condition lasting for about two minutes per seizure. He had been treated with medication that was able to reduce the number of crises per day to between 3 and 7. Also in a good week, he would have only one seizure every third day. He was diagnosed as having a complex epileptic symptomatology.

His IPT treatment consisted of five treatments, each comprising of the following:

1. Enema 900 ml of warm tap water with 100 ml lactulose syrup.
2. Insulin 18 units intravenous bolus.
3. Oral: gamma amino butiric acid (GABA) 100 mg; phenitoin 300 mg, valproic acid (Armstrong) 15 mg and Senokot tablets.
4. Intramuscular: liver extract 0.3 ml; and acetazolamide 50 mg.
5. Intravenous: Vitamin C 1000 mg; calcium gluconate 5 ml; and magnesium sulphate 5 ml.

In between treatments he was given Senoket tablets at bedtime; and Metamucil 11 gms and, daily, acetazolamide 1 tablet a day and phenytoin 3 tablets a day.

After the third IPT treatment the patient recorded the number of seizures per day diminished by 50% and the duration of the seizures was also reduced. After five IPT treatments the patient was discharged and reported as 75% reduction of seizures, over the next 7 months, of seizures that is, the patient reported, after IPT treatment, an average of only one seizure every other week.

Psychiatric Disorders

Case 9: Schizophrenia

A 56 year old male, presented with a ten year history of schitzophrenia, had been diagnosed and treated at a psychiatric hospital in Mexico without results. The family complained of violent behavior of the patient, self-mutilation, insomnia, visual hallucinations and other mental incongruity.

The patient was given four IPT treatments, each comprising:

1. Enema 900 ml of warm tap water with 100 ml lactulose syrup.
2. Insulin 22 units intravenous bolus.
3. Oral: gamma amino butiric acid (GABA) 100 mg; Senokot 6 tablets; and boldodrenal 5 gms. (Infan)
4. Intramuscular: furosemide 20 mg; (Hoechst Rossel) naftidrofuryloxylate 0.05 mg; and cyanacobalamina 1 ml (a form of Vitamin B-12).
5. Intravenous: Vitamin C 500 mg; calcium gluconate 5 ml; dextrovet phosporilate 1 cc (ICN); and dextrose 50% solution 20 cc.

In between treatments he was given 2 Senokot tablets and Metamucil 11 gms at bedtime. Gamma amino butiric acid (GABA), 3 tablets a day.

After the fourth IPT treatment the family of the patient reported the patient was normal again in behavior, there is no known relapse of his condition.

Neoplastic Diseases

In our U.S. Pat. No. 4,971,951 there are set forth four case histories of the application of IPT to various malignacies. These histories are incorporated by reference. IPT has been used across the spectrum of malignant diseases, including cancers of the breast, lung, bone, cervix, prostate, skin, and stomach.

We have found that detoxification, as above described, is an important adjunct to the successful application of IPT in the treatment of neoplastic diseases.

Further, as above noted, we have found that almost all neoplastic diseases are accompanied by an imbalance of the normal ionic or electolytic hierarchy of salts in the bloodstream and, more particularly, we have found that there exists a magnesium ion deficiency in most malignant neoplasisms. As a part of many IPT treatments of cancer, we employ magnesium bromide - 25 mg dissolved in 100 ml distilled water which is administered intravenously in dosages of 1 to 4 ml. We have found magnesium salts are necessary for normal functioning of the central nervous system and are a co-factor for the activation of many enzymatic systems and are needed to counter the ion deficiency associated with most forms of malignancy.

Pulmonary Disorders

Case 10: Asthma

A 65 year old man had suffered for twelve years from coughing and wheezing that occured during winter and spring. His shortness of breath could last for a period of minutes to several hours, sometimes accompanied by a tightness in the chest. When an attack was severe, an audible wheezing would be noticeable. During the two years preceding his treatment by us, he noticed that he was not able to speak more than a few words at a time without taking time to catch his breath. This condition was present during the evenings. He was diagnosed as having bronchial asthma.

He received nine IPT treatments, each comprising the following:

1. Enema 900 ml of warm tap water with 100 ml lactulose syrup.
2. Insulin 18 units intravenous bolus.
3. Oral: terbutaline 2.5 mg; Senokot 2 tablets; and ketotifeno 1 mg.
4. Intramuscular: liver extract 1 ml; and gadital enzyme 1 cc (Italmax).
5. Intravenous: Vitamin C 2 gms; calcium gluconate 5 ml; dexamethasone 4 mg; and amino-phylline 20 mg.

In between treatments he was given at bedtime Senokot and Metamucil 11 gms. He was also given sodium cromolyn 20 mg every 8 hours by inhalation; theophylline once every 8 hours; and Vitamin A 25,000 units daily.

After his discharge, following nine IPT treatments, he has remained completely symptom free for a period of four years, this being through the present (1990).

We have developed certain preparations which have proven to be particularly effective for the treatment of respiratory conditions. One of these comprises a combination of tripsine 6250 UNF, chemotripsine 2500 UNF; guayacol extract 100 mg; theophylline hydroxylated 100 mg; chlorprophenpiridamine 2 mg; and lidocaine chlorohydrate 20 mg. This combination, used as the therapeutic agent in IPT, has been found to have value as anti-inflammatory, bronchodilator, antihistamine and muculytic for respiratory diseases.

Arthritic Diseases

Case 11: Arthritis

An 84 year old woman was seen at our office complaining of severe pain in all of her joints. but, most intensely, at the knees, ankles and wrists. She noticed that the pain increased when there was a change in the humidity. She experienced fatigue, general malaise, low grade fever and, most of the time, she was confined to bed. She also complained of chronic constipation. She had seen several other physicians and received several drugs to treat her condition, but had experienced only passing relief and in no instance had received more than three months of relief from any other treatment.

The patient received eight IPT treatments, each comprising:

1. Insulin 15 units of intravenous bolus.
2. Intravenous Vitamin C 750 mg; calcium gluconate 3 mg; and dextrose 50% 15 cc.
3. Intramuscularly: vitamin B-complex 0.5 ml; neuroflax 0.5 ml (Roussel); and dexamethasone 1 mg.

Orally, during treatment, she received extract of boldo 5 mg; tenoxicam 5 mg; (Roche) and 5 Senokot tablets.

After the above eight treatments the result was a complete remission of her symptoms and she has remained asymptomatic for a period of three years since her treatment.

Case 12: Rheumatoid Arthritis

A 72 year old female had a history of more than 24 years of morning stiffness, pain, swelling of joints in the shoulders, elbows, wrists, fingers and both knees. Some days she could not walk and was confined to bed because of the pain. She was diagnosed as having rheumatoid arthritis. She received treatments from other physicians that sometimes provided up to one year of relief, however, the condition would eventually recur and, as above noted, had recurred over a period of 24 years.

We treated the above patient with IPT, each treatment comprising:

1. Enema 900 ml of warm tap water with 100 ml lactulose syrup.
2. Insulin 18 units intravenous bolus.
3. Intravenous: Vitamin C 500 gms; calcium gluconate 0.5 ml; and dextrovet fosforilado 2 ml.
4. Intramuscular: liver extract 0.5 ml; neuroflax 4 ml; and voltaren 75 mg (Ciba-Geigy).
5. Oral: d-penicillin 250 mg; metronidazole 250 mg; aspirin 1000 mg; and 2 Senokot tablets.

In between treatments she was given at bedtime 2 Senokot tablets and Metamucil 11 gms. She was also given d-penicillin 250 mg every 8 hours and tenoxicam 20 mg (Roche) every day. After the fourth IPT treatment the patient was able to walk without pain in either knee and suffered from no morning stiffness. She felt more energy and was able to move both arms and was able to button her shirt and dress. She has remained symptom free for a period of six years. After six years, she received, upon a slight reoccurrence of symptoms, another IPT treatment and then remained symptom free for a period of four more years up through and including the present (1990).

Case 13: Rheumatic Fever/Bacterial Infections

A 10 year old girl was seen at our office complaining of severe pain in all of her joints but, most intensely, in the knees and ankles. As such she was forced to spend much of her time resting in bed. She also experienced fatigue, general malaise, low grade fever, and painful swelling of her joints. She had seen several other physicians and received several drugs to treat inflamed tonsils but her mother stated that her daughter had not improved at all. A lab test showed a presence of high serum levels of streptococcal antibodies ASQ and positive for strepococcus Group A. The condition was a form of rheumatic fever.

She received five IPT treatments each comprising the following:

1. Five units insulin intravenous bolus.
2. Intravenous Vitamin C 100 mg; calcium gluconate 1 mg; and dextrose 50% solution 10 cc.
3. Intramuscular: liver extract 0.3 cc; naftidrofuryloxylate 0.3 cc; furosemide 5 mg; neuroflax 0.3 cc (Roussel); voltaren 0.3 cc (Ciba-Geigy); and penicillin G 300,000 units.
4. Orally: extract boldo 5 mg; acetaminophen 40 mg; tenoxicam 1 mg (Roche); and Senokot 1 tablet.

These treatments resulted in the complete remission of her symptoms. A lab test thereafter reported negative as to the streptococcus. No recurrance has occurred.

Musculoskeletal Diseases

Case 14: Osteomyelitis

A 64 year old female was presented with acute onset of pain in her left elbow and a fever of 106 F. She also noticed a tenderness over her left arm and elbow in which any movement produced pain. Some weeks she would also experience a sore throat up to nine days at a time. She was diagnosed as having osteomyelitis.

Her IPT treatment consisted of three IPT treatments, each comprising:

1. Enema 900 ml of warm tap water with 100 ml lactulose syrup.
2. Insulin 17 units intravenous bolus.
3. Intravenous: administration of vitamin C 1000 mg; calcium gluconate 5 ml; and dextravit phosforalo 2 ml (ICN).
4. Intramuscular: liver extract 0.3 cc; Neuroflax 4 ml (Roussel); and penicillin G 600,000 units.
5. Oral: ibuprofen 275 mg and 2 Senokot tablets.

In between treatments she was given in the evenings two Senokot tablets and 11 gms Metamucil. She was also given erythromycin 250 mg every 6 hours and tenoxicam 20 mg (Roche), once a day.

After the third IPT treatment the patient was able to move her elbow without pain and has remained symptom free for a number of years.

The product Neuroflax, above referred to, is a combination of cobabamide 2 mg and tiocolchicosi 4 mg. This combination is most valuable across a broad range of anti-inflammatory, anti-rheumatic and analgesic usages. Also, in such areas, we have used combinations of aspirin 325 mg, aluminum hydroxide 150 mg and magnesium hydroxide 150 mg. We have also found the drug tenoxicam to be most useful in this area, as is sodium dichloroethanate known commercially as voltaren (Ciba-Geigy).

Urologic Disorders

Case 15: Diabetes

A 58 year old hispanic male was presented with a four year history of diabetes which was controlled with a low sugar diet and oral hypoglycemic agent. Three days before his visit to our office, he had an acute pain in the left side of his chest lasting 45 minutes, and also involving the left arm. He further noticed abdominal discomfort. He further noticed a decrease in size and force of his urinary stream, a sensation of incomplete emptying of his bladder, and no erection or sexual desire. His glucose blood level was measured at 276 mg/percent and an EKG revealed a right bundle blockage. He also had poor eyesight.

The patient received four IPT treatments, each comprising:

1. Enema 900 ml of warm tap water with 100 ml lactulose syrup.
2. Insulin 20 units intravenous bolus.
3. Intravenous: Vitamin C 1000 mg; calcium gluconate 5 ml; dextavit phosforilato 1 cc; and dextrose 50% solution 20 cc (ICN).
4. Intramuscular: liver extract 1 cc and cynacobalamin 1 cc.
5. Oral: selenium 50 mg; zinc 100 mg; Adalat tablets (Bayar); 3 Senokot tablets; and aspirin 900 mg.
6. A 10 mg disc of nitroglycerin was placed upon his chest.

In between treatments he was given in the evening Senokot tablets and Metamucil 11 mg. He was further given adalat tablets (1) every 8 hours, zinc 50 mg every 12 hours, tolbutamide 1 tablet per day; and aspirin 300 mg once a day.

At the end of the first IPT treatment the patient reported improvement in his eyesight. After the second treatment he noticed his urine flow was more uniform. After the third IPT treatment his sexual desire had improved and noticed some erection. Following the fourth IPT treatment he reported his erection was near normal.

A test of his blood reported glucose at a level of 135 mg/percent, a great improvement. His EKG was unchanged.

We have found IPT to be most effective in the treatment of a variety of urinary disorders. In connection therewith we have used medications including nylidrine hydrochloride and the combination of nalidixic acid 500 mg and penazopyridine 50 mg tablets.

In the treatment of diseases of the prostate we have found to be most useful hydrosoluble dealbuminated extract and pygmeum africanum cortex extract.

Viral Diseases

Case 16: Herpes

A 42 year old male had developed malaise, chills and fever and a temperature of 101° F. for a period of three days. On the fourth day he noticed the appearance of vesicles in the left side of his trunk, with severe pain. After seven days the vesicles had dried and all symptoms disappeared. However, four months later he had another crisis that lasted the same duration. He sought medical attention with only partial results. He related that he had had this condition for three years with recurrences every four to six months.

He was diagnosed as having herpes simplex virus.

He received four IPT treatments, each comprising:

1. Enema 900 ml of warm tap water with 100 ml lactulose syrup.
2. Insulin 24 units intravenous bolus.
3. Intravenous: Vitamin C 1000 gms; calcium gluconate 5 ml; vitamin B complex 1 ml; and ribavirin 100 mg (ICN).
4. Oral: aspirin 600 mg; clemizole 20 mg (Schering Plough); dextropropoxiphene 65 mg.
5. Intramuscular: liver extract 1 ml.

In between treatments he was given aspirin 6 mg every 8 hours; ribavirin 50 mg (ICN), and in the evening 2 Senokot tablets and 1 tablet vitamin B complex.

After his discharge, the following four IPT treatments, he remained symptom free for a period of two years. At that point he had another acute attack and received three further IPT treatments. Thereafter he remained symptom free for a period of 8 years continuing through the present (1990).

It is to be understood that the term "insulin" as used herein includes those biologically active peptides known as "insulin-mimickers" and that the term "glucose" encompasses related sugar molecules such as dextrose.

Numerous modifications and variations of the present invention are possible in light of the above teaching, and therefore, within the scope of the appended claims, the invention may be practiced otherwise than as particularly described.

Having thus described my invention what I claim as new, useful and non-obvious and, accordingly, secure by Letters Patent of the United States is:

1. A method for potentiation of a therapeutic agent, comprising the steps of:
    (a) administering an effective dose of insulin to induce a hypoglycemia;
    (b) administering an effective dose of a therapeutic agent; and
    (c) administering an effective dose of glucose sufficient to substantially neutralize said hypoglycemia.

2. The method as recited in claim 1, in which said agent administering step comprises:
    the step of intravenously administering said therapeutic agent in a sequence after said hypoglycemia has been induced.

3. The method as recited in claim 1 in which said therapeutic agent administering step comprises:
    the step selected from the group consisting of: oral administration, intramuscular administration, subcutaneous vaginal administration, rectal administration, ocular administration, respiratory administration, transdermal administration, sublingual administration and nasal administration.

4. The method as recited in claim 3 in which said therapeutic agent administering step comprises the step of:
    in the case of a more slowly metabolically absorbed agent, administration of said therapeutic agent prior to said insulin administration step so that the level of such agent in the blood is optimized by the time that said hypoglycemia is induced following said insulin administering step.

5. The method as recited in claim 3 in which said step of administering a therapeutic agent comprises the step of:
    administering said therapeutic agent contemporaneously with said insulin administration.

6. The method as recited in claim 3 in which the step of administering said therapeutic agent comprises the step of:
    in the case of a more rapidly metabolically absorbed agent, administering said therapeutic agent subsequent to the onset of said hypoglycemia.

7. The method as recited in claim 6 in which said step of administering said glucose comprises the step of:
    contemporaneously administering said glucose with said administration of said therapeutic agent.

8. The method as recited in claim 1 in which said step of insulin administration comprises the step of:
   administration of in the range of about one to about four units of insulin per ten kilograms of body weight.

9. The method as recited in claim 2 in which said step of insulin administration comprises the step of:
   administration of in the range of about one to about four units of insulin per ten kilograms of body weight.

10. The method as recited in claim 3 in which said step of insulin administration comprises the step of:
    administration of in the range of about one to about four units of insulin per ten kilograms of body weight.

11. The method as recited in claim 8 in which said step of glucose administration comprises the step of:
    administering between about ten and about one hundred cubic centimeters of between about five and about fifty percent hypertonic glucose solution.

12. The method as recited in claim 9 in which said glucose administering step comprises the step of:
    administration of between about ten and about one-hundred cubic centimeters of between about five and about fifty percent hypertonic glucose solution.

13. The method as recited in claim 10 in which said step of glucose administration comprises the step of:
    administration of between about ten and about one-hundred cubic centimeters of between about five percent and about fifty percent hypertonic glucose solution.

14. The method as recited in claim 1 in which said therapeutic agent administering step includes the step of administration of a therapeutic agent selected from therapeutic agents of this group consisting of agents that exhibit actions of the following types:
    anti-viral, anti-bacterial, anti-neoplastic, antiseptic, antibiotic, immunological, nutritional, monoclonal, psychoactive, neurologic, anti-cholesterol, cardiovascular, gastro-intestinal, respiratory, anti-arthritic, analgesic, dermatological, gynecologic, fertility inducing, impotence treating, urinary tract treating, muscular, antihistamine, hepatic treating, antispasmodic, vascular dilation, anti-inflammatory, enzymatic, electrolytic, neuromuscular, hormonal oxygenating, de-toxifying, corticosteroidal and hematopietic.

15. The method as recited in claim 1 further comprising the step of administration of a cathartic prior to said insulin administration step.

16. The method as recited in claim 15, further comprising the step of administration of a nutrient solution after said cathartic administration step and prior to said insulin administration step.

17. The method as recited in claim 15, further comprising the step of administration of oxygen after said cathartic administration step.

18. The method as recited in claim 11, further comprising the step of administration of oxygen.

19. The method as recited in claim 17 in which said oxygen administration step comprises:
    the step of administration of between about three thousand and about five thousand cubic centimeters per minute of oxygen administered for between about five and about ten minutes.

20. The method as recited in claim 18 in which said step of oxygen administration comprises the step of:
    the step of administering oxygen at the rate of between about three thousand and about five thousand cubic centimeters second for a period of between about five minutes and about ten minutes.

21. The method as recited in claim 1 in which said agent administration step comprises:
    the step of administration of said therapeutic agent when said hypoglymia has been induced.

22. The method as recited in claim 3, which said therapeutic administration step occurs subsequent to said insulin administration step but prior to onset of said hypoglycemia.

23. An adjuvant system for human use, the system comprising:
    (a) a quantity of insulin in the range of about one to about four units per ten kilograms of body weight;
    (b) a pre-determined quantity of a therapeutic agent; and
    (c) glucose in the form of a hypertonic solution in the range of between about five percent and about fifty percent glucose, the volume of said solution being in the range of about ten cubic centimeters to about one hundred cubic centimeters.

24. The system as recited in claim 23 in which said therapeutic agent is selected from therapeutic agents of the group consisting of agents that are:
    anti-viral, anti-bacterial, anti-neoplastic, antiseptic, antibiotic, immunological, nutritional, monoclonal, psychoactive, neurologic, anti-cholesterol, cardiovascular, gastro-intestinal, respiratory, anti-arthritic, analgesic, dermatological, gynecologic, fertility inducing, impotence treating, urinary tract treating, muscular, antihistamine, hepatic treating, antispasmodic, vascular dilation, anti-inflammatory, enzymatic, electrolytic, neuromuscular, hormonal oxygenating, de-toxifying, corticosteroidal and hematopietic.

25. The system as recited in claim 24 in which said therapeutic agent comprises oxygen.

26. The system as recited in claim 24 in which said therapeutic agent includes oxygen.

27. The system as recited in claim 23, further comprising:
    a cathartic.

28. The system as recited in claim 27 in which said system further comprises oxygen.

29. The system as recited in claim 25 in which said oxygen comprises between about three thousand and about five thousand cubic centimeters per second of respiratory oxygen consumed for between about five and about ten minutes.

30. The system as recited in claim 26 in which said oxygen comprises between about three thousand and about five thousand cubic centimeters per second of respiratory oxygen consumed for between about five and about ten minutes.

31. The system as recited in claim 28, in which said oxygen comprises between about three thousand and about five thousand cubic centimeters per second of respiratory oxygen consumed for between about five and about ten minutes.

* * * * *